(12) United States Patent
Kratoska et al.

(10) Patent No.: US 8,652,134 B2
(45) Date of Patent: Feb. 18, 2014

(54) SINGLE-USE ELECTRONIC APPARATUS HAVING A THERMAL SWITCH

(75) Inventors: William F. Kratoska, Plymouth, MN (US); Kester J. Batchelor, Minneapolis, MN (US)

(73) Assignee: Gyrus Medical, Inc., Maple Grove, MN (US)

( * ) Notice: Subject to any disclaimer, the term of this patent is extended or adjusted under 35 U.S.C. 154(b) by 497 days.

(21) Appl. No.: 13/023,092

(22) Filed: Feb. 8, 2011

(65) Prior Publication Data

US 2012/0203224 A1   Aug. 9, 2012

(51) Int. Cl.
*A61B 18/12*   (2006.01)
*A61B 18/10*   (2006.01)

(52) U.S. Cl.
USPC ............... 606/42; 606/32; 606/34; 606/40; 606/41; 604/95.05

(58) Field of Classification Search
USPC .................... 606/32–50; 604/95.05
See application file for complete search history.

(56) References Cited

U.S. PATENT DOCUMENTS

| | | | |
|---|---|---|---|
| 4,951,690 A | 8/1990 | Baker | |
| 5,573,533 A | 11/1996 | Strul | |
| 6,611,793 B1 | 8/2003 | Burnside et al. | |
| 7,045,557 B2 | 5/2006 | Jin et al. | |
| 7,118,564 B2 | 10/2006 | Ritchie et al. | |
| 7,236,827 B2 | 6/2007 | Vitt et al. | |
| 7,585,295 B2 | 9/2009 | Ben-Nun | |
| 7,785,277 B2 | 8/2010 | Babaev et al. | |
| 2003/0097125 A1* | 5/2003 | Hall | 606/34 |
| 2004/0087832 A1 | 5/2004 | Glukhovsky et al. | |
| 2005/0284773 A1 | 12/2005 | Allen | |
| 2008/0205481 A1 | 8/2008 | Faries et al. | |
| 2008/0281310 A1* | 11/2008 | Dunning et al. | 606/32 |
| 2008/0281311 A1 | 11/2008 | Dunning et al. | |
| 2009/0050253 A1 | 2/2009 | Thomas et al. | |

FOREIGN PATENT DOCUMENTS

| | | |
|---|---|---|
| EP | 0 062 846 A1 | 10/1982 |
| WO | WO 98/37819 | 9/1998 |

OTHER PUBLICATIONS

Mar. 9, 2012 International Search Report for International Application No. PCT/US2011/062633.
Mar. 9, 2012 Written Opinion of the International Searching Authority for International Application No. PCT/US2011/062633.

* cited by examiner

*Primary Examiner* — Michael Peffley
*Assistant Examiner* — Khadijeh Vahdat
(74) *Attorney, Agent, or Firm* — Oliff, PLC

(57) ABSTRACT

An electronic apparatus includes a circuit portion that is configured to control an operation of the electronic apparatus and a heat-activated mechanical switch including, for example, a shape-memory material. The shape-memory material has a property such that the shape-memory material assumes a predetermined shape when the electronic apparatus is heated to a transition temperature. The shape-memory material disables the apparatus by acting on the circuit portion when the shape-memory material assumes the predetermined shape.

20 Claims, 6 Drawing Sheets

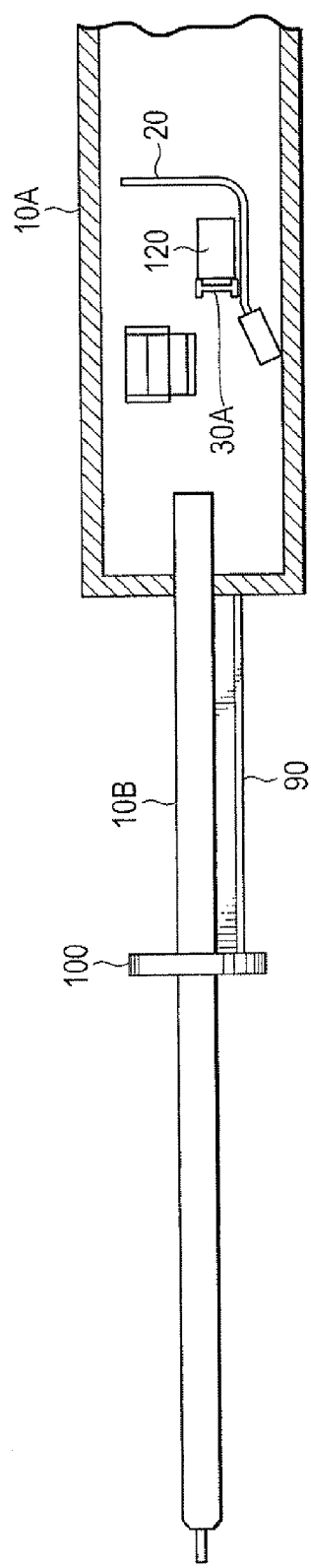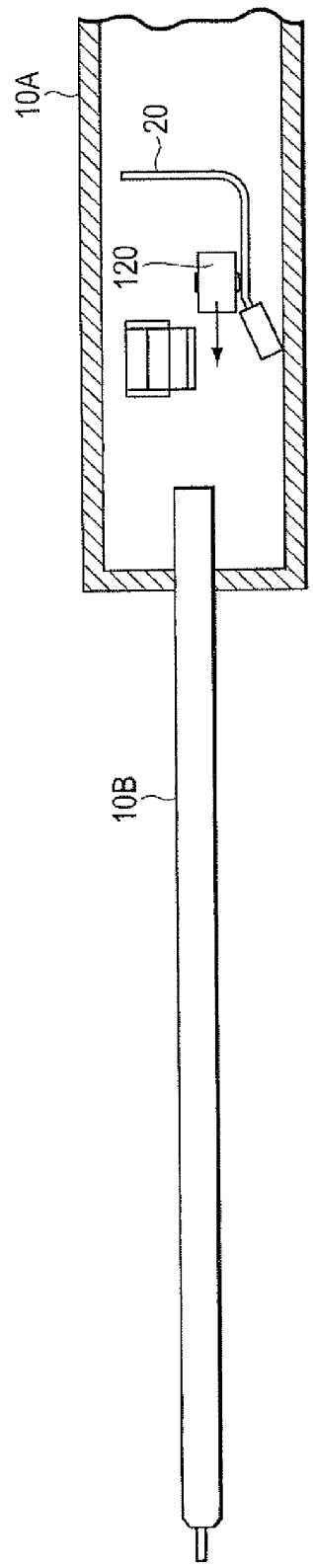

SINGLE-USE ELECTRONIC APPARATUS HAVING A THERMAL SWITCH

BACKGROUND

1. Field of the Invention

This invention relates to disposable single-use devices, which can be, for example, electronic surgical apparatus such as an electrosurgical or electrocautery device. In particular, this invention relates to such devices that include a thermal switch configured to electronically disable a single-use apparatus so that it cannot be used a second time.

2. Background of the Invention

Medical devices such as, for example, electrosurgery and electrocautery devices, may be used to, for example, cut living organic tissue. The cutting action is accomplished by inserting a distal end of the device into the tissue. These devices may also be used to cauterize tissue surrounding the distal end of the device, thereby coagulating blood in the surrounding tissue.

Over time, the requirements to maintain a sterile operating field during the use of such medical devices have become more stringent. This has led to a great number of medical devices such as, for example, electrosurgical or electrocautery devices, being manufactured as single use disposable items, rather than items that are resterilized and reused. In addition to reducing the transmission of organisms and infectious agents, this change has also led to surgical products performing more reliably and consistently. Reusable products that are sometimes old, often cleaned properly, often repaired properly, but always with a different history will always be less reliable and consistent than new, essentially identical products. For this reason, many medical devices are manufactured with the intent that they will be used a single time. Device manufacturers also do testing that very accurately characterizes performance of a device over a limited life span that is impossible over an extended life span.

A disadvantage of the change to single-use disposable items is that the cost of any medical procedure is increased. In response to this increased cost, some medical facilities have begun reusing medical devices that were designed for one use. For the medical facility, the cost of a procedure will drop while reimbursement stays the same. However, the patient bears an additional risk of transmittable disease and the physician bears additional risk of liability, both usually without knowing that used devices were being provided. The device company also bears additional liability. In addition, reused devices that perform poorly or are more prone to failure still have the manufacturer's name on them, damaging its reputation.

Some single-use devices include circuitry to detect whether the device has been used and will disable the device when a use has been detected. Other devices, such as that disclosed in U.S. Pat. No. 7,045,557, include a weak link such that the device will stand up to extended one time use, but will degrade quickly and obviously afterwards. Alternatively, some devices are designed such that the geometry of the device makes the device more difficult to properly clean and reprocess.

However, existing devices that employ the single use methods discussed above still can suffer from the above-mentioned problems associated with reprocessing.

Therefore, in view of the above-mentioned problems associated with reusing/reprocessing single-use electronic apparatus, it is desirable to develop a way of effectively disabling a single-use electronic apparatus in an efficient and cost effective manner.

SUMMARY OF THE INVENTION

In view of the above, it is desirable to provide an electronic apparatus, for example, a surgical apparatus that includes a circuit portion that may be configured to control an operation of the apparatus, and a shape-memory material. The shape-memory material may have a property such that the shape-memory material assumes a predetermined shape when the apparatus is heated to a transition temperature. The shape-memory material may disable the apparatus by acting on the circuit portion when the shape-memory material assumes the predetermined shape. According to some embodiments, the shape-memory material may be nitinol.

In one embodiment, the shape-memory material may be configured such that, upon assuming the predetermined shape, the shape-memory material opens a circuit in the circuit portion to disable the apparatus.

In another embodiment, the shape-memory material may be configured such that, upon assuming the predetermined shape, the shape-memory material completes a circuit in the circuit portion to disable the apparatus.

In a further embodiment, the transition temperature may be below a sterilization temperature of the apparatus. Accordingly, sterilization of the apparatus after its first use will cause the apparatus to become disabled.

In yet another embodiment, the electronic apparatus may include a movable blocking element that may be disposed adjacent to the shape-memory material and extends out of the electronic apparatus. The movable blocking element may be configured to block the shape-memory material from assuming the predetermined shape prior to moving the movable blocking element from a blocking position. Accordingly, the apparatus can be sterilized before its first use without disabling the apparatus.

In another embodiment, the movable blocking element may be attached to a packaging of the electronic apparatus such that the movable blocking element is moved from the blocking position upon removing the electronic apparatus from the packaging. Accordingly, the apparatus cannot be inadvertently disabled before it is removed from its packaging.

In yet another embodiment, the movable blocking element may include an elongated portion that inhibits use of the electronic apparatus if the movable blocking element is not removed from the electronic apparatus prior to use. This ensures that the movable blocking element will be removed before the apparatus is used, thus ensuring that the apparatus will become disabled after its first use when the shape-memory material is heated to its transition temperature.

In another embodiment, the electronic apparatus may be an electrosurgical device that includes a shaft portion. The elongated portion of the movable blocking element may include a ring like portion that is disposed at least partially around the shaft portion. As an alternative, or in addition to the ring-like portion, the elongated portion of the movable blocking element may have a flange portion that is configured to inhibit operation of an operation button of the electronic apparatus prior to removal of the movable blocking element from the electronic apparatus.

At least a portion of the movable blocking element may be flexible, and a removal path of the movable blocking element may be non-linear, thereby making reinsertion of the movable blocking element after removal virtually impossible.

In another embodiment, the electronic apparatus may have at least one movable portion that moves to a blocked position to block return of the movable blocking element to the blocking position after the movable blocking element has been removed from the blocking position. This also makes it virtually impossible to reinsert the movable blocking element after it has been removed.

At least one portion of the movable blocking element may be a pin that is removed from the apparatus when the pin is moved out of the blocking position.

The electronic surgical apparatus may apply heat to tissue, and the circuit portion may include a heat-controlling circuit of the apparatus. In addition, the electronic surgical apparatus may cut tissue, and the circuit portion may include a cutting-controlling circuit of the electronic surgical apparatus. The apparatus is disabled because the heat-controlling and/or cutting-controlling circuit(s) is/are disabled by the shape-memory material.

In another embodiment, the single-use electronic apparatus may include a circuit portion that is configured to control an operation of the electronic apparatus. The single-use electronic apparatus may include a shape-memory material having a property such that the shape-memory material assumes a predetermined shape when the electronic apparatus is heated to a transition temperature. The apparatus may also include a signal transmitting portion. The shape-memory material may disable the apparatus by acting on the circuit portion when the shape-memory material assumes the predetermined shape. The signal transmitting portion may send a signal to a display unit to indicate that the single-use electronic apparatus is disabled due to being reprocessed after the shape-memory material assumes the predetermined shape.

BRIEF DESCRIPTION OF THE DRAWINGS

FIG. 5 is a simplified view of an embodiment prior to the blocking element being removed.

FIG. 6 is a simplified view of an embodiment in which the blocking element is removed and a movable portion blocks reentry of the blocking element.

DETAILED DESCRIPTION

Figure 1:
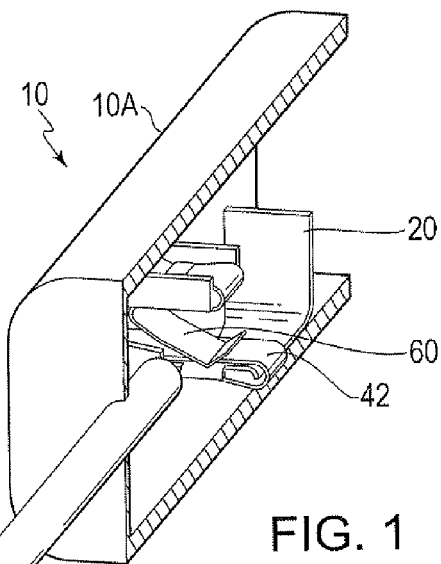
FIG. 1 is a simplified perspective view of an electronic apparatus in a state where the shape-memory material has assumed the predetermined shape.

FIG. 1 is a simplified perspective view of a single-use device 10 according to one embodiment. The single-use device 10 includes a housing 10A and a shaft 10B connected to the housing 10A. The single-use device 10 includes a shape-memory material 20 and a circuit portion 40 (see FIG. 8). The shape-memory material 20 and the circuit portion 40 are housed in the housing 10A. Shape-memory materials are materials that undergo a molecular structure phase change within a certain temperature range. When the phase changes in a shape-memory material, a physical property of the shape-memory material changes drastically. The shape-memory material 20 illustrated in FIG. 1 assumes a predetermined shape when heated to or above a transition temperature. When the shape-memory material 20 is below its transition temperature, it can be bent into various shapes. The shape-memory material 20 will stay in the shape into which it is bent until it is heated to or above its transition temperature. When heated to or above its transition temperature, the shape-memory material 20 will return to its predetermined shape.

The shape-memory material 20 is preferably made of nitinol. Nitinol is easily deformable below its transition temperature. However, once subjected to a temperature above the transition temperature, nitinol is very spring-like and will revert back to its original (i.e., predetermined) shape even if it had been previously deformed while at a temperature below its transition temperature. Nitinol has a transition temperature range that can be controlled to any point within a wide range. When the shape-memory material is made of nitinol, it is preferred that the nitinol is configured so as to have a transition temperature ranging between about 100° F. and about 105° F. It is desirable to set the transition temperature range so that it is not too low to avoid prematurely disabling the single-use device 10 during a normal, first-time use. In particular, for single-use electrosurgical devices, due to the user's body temperature and electrical heating, it is conceivable that the device handle could reach 90° F. during a normal first-time use. Therefore, it is desirable that the transition temperature range at least be above 90° F. Likewise, it is desirable to not raise the transition temperature range too high to ensure that resterilization of a used single-use device 10 will disable it. Ethylene Oxide (ETO) sterilization is a common form of sterilization that can take place at various temperatures. Most commonly, ETO sterilization takes place between 104° F. and 140° F. Although ETO sterilization can be conducted as low as 86° F., there are disadvantages to sterilization cycles below approximately 110° F. As such, it is desirable to provide nitinol with a transition temperature ranging between about 100° F. and about 105° F. The shape-memory material 20 can be made of any suitable material that assumes a predetermined shape upon heating to or above a transition temperature.

The embodiment illustrated in FIG. 1 illustrates a state of the shape-memory material 20 in which the shape-memory material 20 has been subjected to the transition temperature causing the shape-memory material 20 to bend upward (to its predetermined shape) to act on the circuit portion 40 and thus disable the apparatus 10. The shape-memory material 20 can disable the apparatus 10 by either making (closing) or breaking (opening) a disabling/enabling circuit in the circuit portion 40. The disabling/enabling circuit disables/enables the circuit portion 40 or functions of the circuit portion 40 in whole or part. When the device is an electrosurgical device, the circuit or the function that becomes disabled by closing or opening the disabling/enabling circuit could be a circuit or a function that controls cutting, heating or both. The embodiment illustrated in FIG. 1 shows the shape-memory material 20 bending up to make an electrical circuit by causing a contact 42 attached to the shape-memory material 20 to contact a contact portion 60. In a different embodiment, heating the shape-memory material 20 to or above its transition temperature could cause the shape-memory material 20 to assume a predetermined position in which the contact 42 moves away from the contact portion 60 to open the circuit. A distal portion of the shape-memory material 20 itself may form a contact for the purposes of disabling the circuit portion, thus not requiring a separate contact such as contact 42. That is, the shape-memory material can be part of the circuit (and be electrically conductive) or simply move electrically conductive parts of the circuit. Of course, wiring and/or electrical lines also are electrically attached to (associated with) the contact 42 and the contact portion 60 so as to incorporate them into a circuit. The shape-memory material 20 may also trigger a different output to a generator 140 (see FIG. 8) to cause the generator 140 to indicate that the single-use device has been reprocessed and will no longer function. This alerts users to the fact that the apparatus has been reprocessed and is unusable so that the user does not believe that the apparatus is defective.

Figure 2:
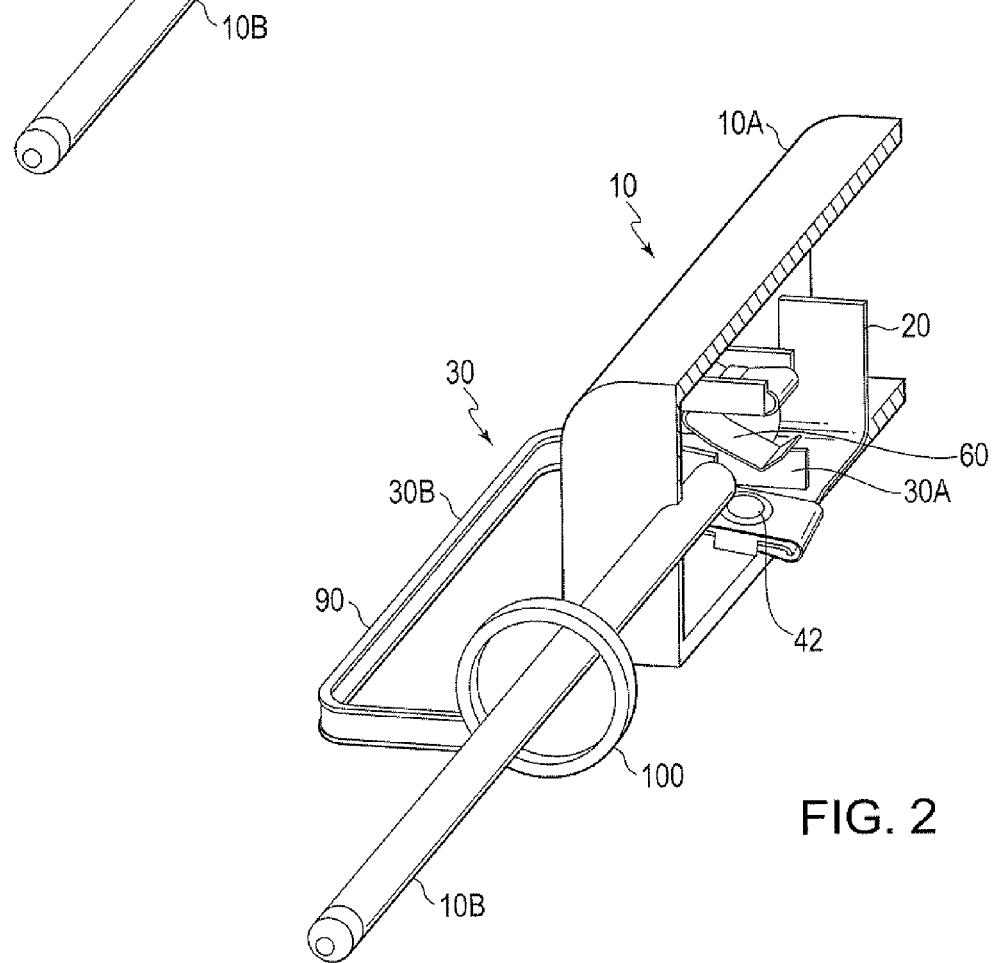
FIG. 2 is a simplified perspective view according to another embodiment in which a pin and extending portion are included to block movement of the shape-memory material until the pin has been removed.

FIG. 2 illustrates a state of the shape-memory material 20 in which the shape-memory material 20 has not been subjected to the transition temperature. As seen in FIG. 2, because the shape-memory material 20 is in an unbent state (i.e., has not been subjected to the transition temperature), the contact 42 is separated from the contact portion 60.

Reprocessing is not the first time that the single-use device 10 may be subjected to a temperature above the transition temperature. For example, the single-use device 10 may be subjected to a temperature above the transition temperature during storage or transportation of the single-use device 10. In addition, the single-use device 10 may be subjected to an initial sterilization process in which a temperature exceeds the transition temperature prior to its first use. Accordingly, it is desirable to provide a way of preventing the single-use device 10 from being disabled prematurely.

FIG. 2 illustrates an embodiment of the single-use device 10 in which a blocking element 30 is provided to hold the shape-memory material 20 in an initial position. The blocking element 30 includes a pin 30A and an elongate portion 30B. In the initial position, the pin 30A is inserted into housing 10A and disposed adjacent to the shape-memory material 20, between the contact 42 and the contact portion 60. In a different embodiment, the pin 30A is disposed adjacent to the shape-memory material 20 so that the contact 42 cannot move away from the contact portion 60 to open the circuit. In so doing, pin 30A prevents the shape-memory material 20 from bending and assuming its predetermined shape prematurely even if it is sterilized and thus heated above its transition temperature. The blocking element 30 is preferably configured such that a user is compelled to remove the pin 30A prior to a first use of the single-use device 10. The embodiment in FIG. 2 includes an elongated portion 30B comprising a strap 90 and an end portion 100 in the form of a ring. The elongate portion 30B extends out of the housing 10A. The elongate portion 3013 is connected to the pin 30A. The strap 90 connects the pin 30A and the end portion 100. The strap 90 and the end portion 100 make it so the user must remove the pin 30A with the elongate portion 30B prior to use because the ring-like end portion 100 gets in the way. The end portion 100 in FIG. 2 is illustrated as a ring that surrounds the shaft 10B. However, the end portion 100 can have any configuration including a square, triangle etc. at least partially around the shaft 10B so long as the end portion 100 deters a user from using the single-use device 10 prior to removing the pin 30A with the elongate portion 30B.

Figure 3:
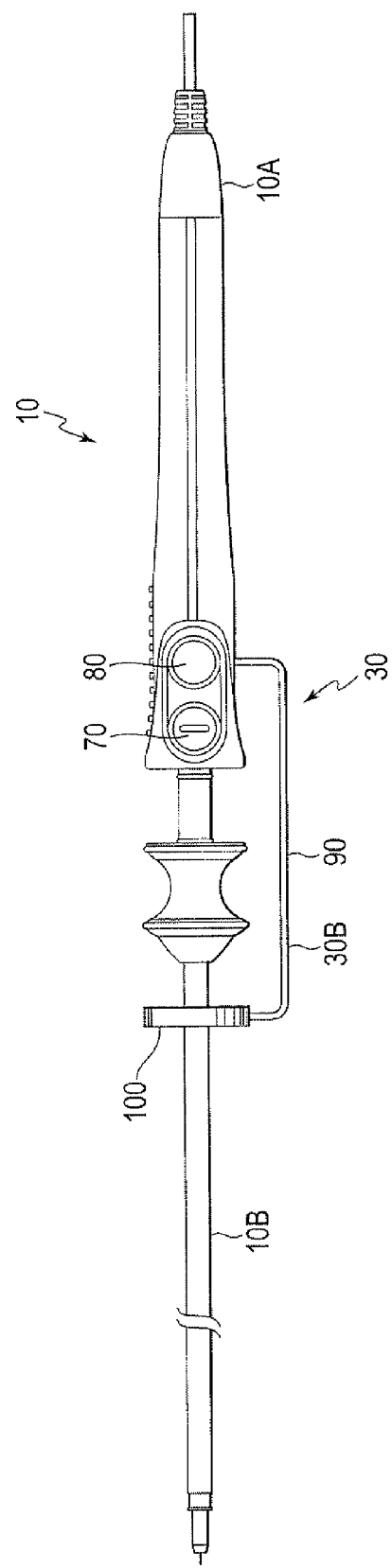
FIG. 3 is a planar top view of the device of FIG. 2.
Figure 7:
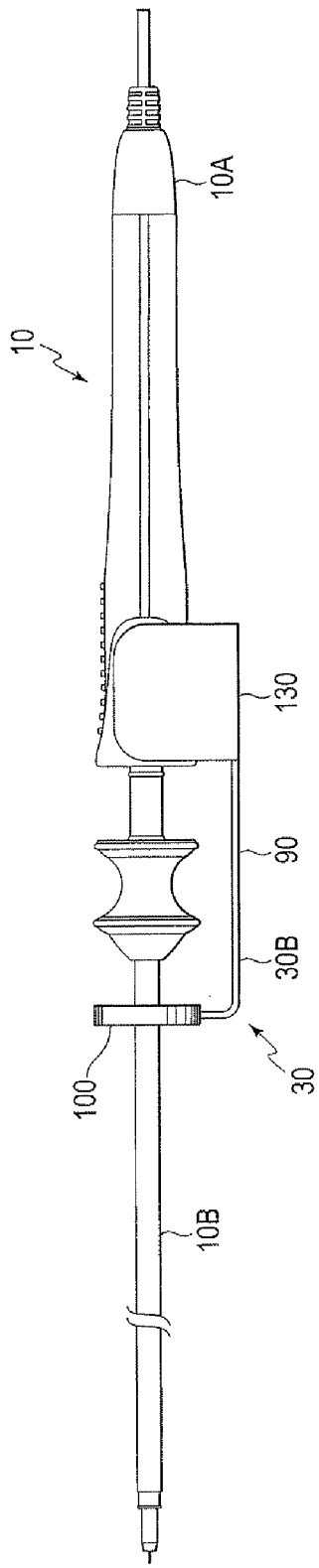
FIG. 7 illustrates an embodiment in which flange portions cover cut and coagulation buttons.

FIG. 3 illustrates a plan view of the FIG. 2 embodiment in which the single-use device 10 is an electrosurgical apparatus. The single-use device 10 is not limited to any particular type of medical device, and can be any type of device in any field of endeavor where it is desirable to disable the device after a first use. As seen in FIG. 3, the single-use device 10 includes a cut button 70 and a coagulation button 80. FIG. 7 illustrates another embodiment in which the elongated portion 30B includes flange portion 130 that extends over and blocks use of the cut button 70 and the coagulation button 80 prior to the pin 30A being removed with the elongated portion 30B. There could be a separate flange for each button 70/80 instead of the single flange 130. The flange 130 is simply an alternative or additional way of causing the user to remove the pin 30A with the elongated portion 30B prior to use. The flange 130 could be used without the end portion 100.

Figure 4:
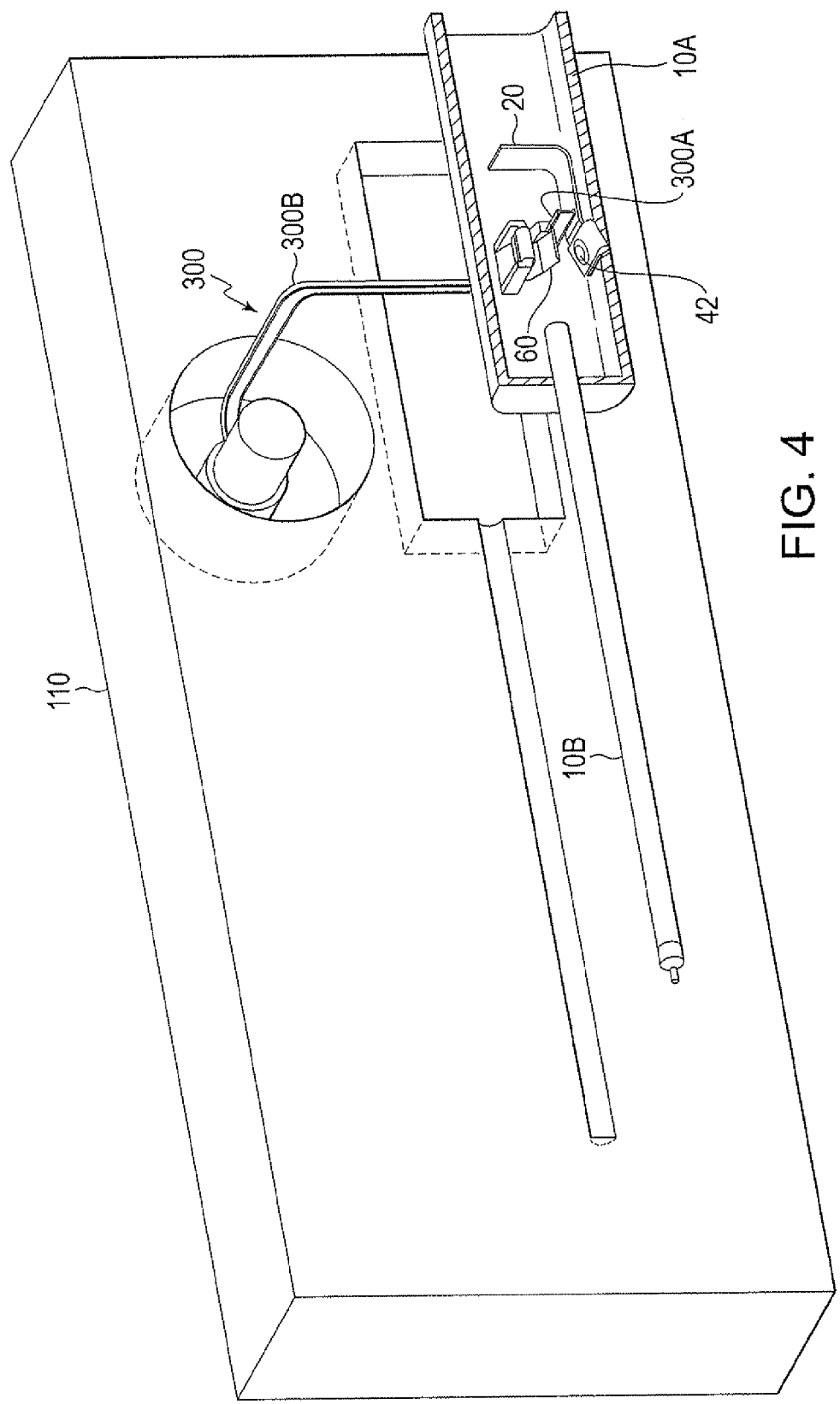
FIG. 4 is a simplified view of the apparatus according to one embodiment in which the pin is attached to a packaging of the apparatus.

FIG. 4 illustrates another embodiment in which a blocking element 300 is attached to a packaging 110 of the single-use device 10. The blocking element 300 includes a pin 300A same as the pin 30A and an elongated portion 300B. The elongated portion 300B extends out of the housing 10A. The elongated portion 300B connects the pin 300A and the packaging 110. As such, the pin 30A is necessarily removed upon removing the single-use device 10 from the packaging 110. The device 10 would be sterilized before it is removed from its packaging 110.

Figure 9:
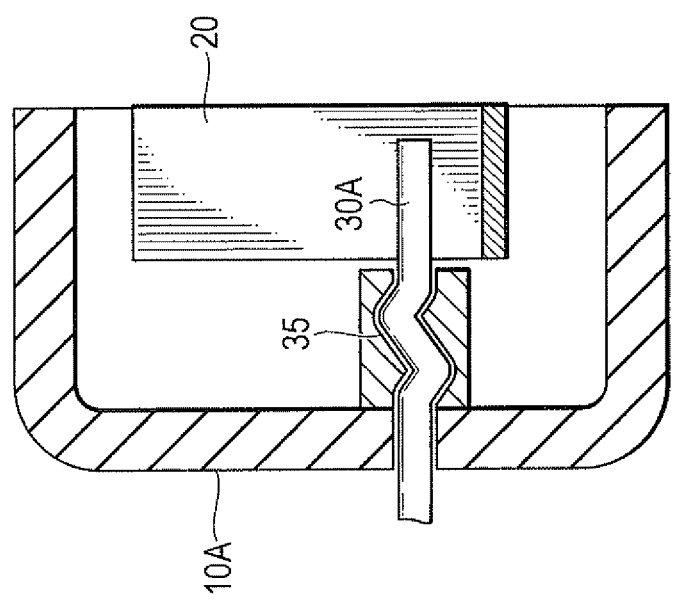
FIG. 9 is a simplified diagram illustrating one embodiment in which a removal path of the blocking element is winding in nature to inhibit reentry of the blocking element.

FIGS. 5 and 6 illustrate another embodiment in which a movable portion 120 is provided. The movable portion 120 is biased against the pin 30A such that, upon removal of the pin 30A, the movable portion 120 moves over an exit hole of the pin 30A so as to block and make impossible reentry of the pin 30A. The movable portion 120 can be biased against the pin 30A by means of a spring or by means of the movable portion 120 being elastic. FIG. 5 illustrates a state in which the pin 30A is provided in the single-use device 10. FIG. 6 illustrates a state in which the pin 30A has been removed and the movable portion 120 has moved into a blocked position at least partially covering the exit hole of the pin 30A. Alternatively, as illustrated in FIG. 9, at least a portion of the pin 30A may be flexible, and an exit path 35 of the pin may be winding in nature, thereby making reinsertion of the pin 30A difficult or impossible. The movable portion 120 or winding passage, etc. make it very difficult for refurbishing companies to "reset" the device into a state where it will be operative and able to be used after sterilization.

Figure 8:
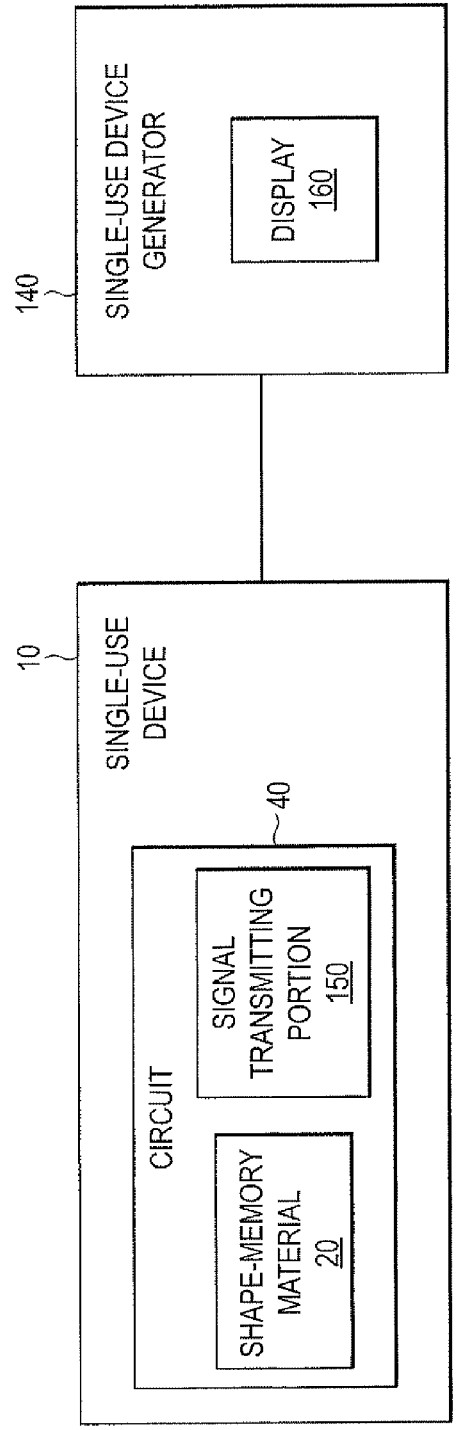
FIG. 8 is a schematic diagram of the apparatus according to one embodiment.

FIG. 8 illustrates a schematic diagram of the single-use device 10 according to one embodiment. In addition to the embodiment described above, in the embodiment illustrated in FIG. 8, the circuit 40 further includes a signal transmitting portion 150. This embodiment illustrates a preferred embodiment in which, upon assuming the predetermined shape, the shape-memory material 20 closes a normally open circuit. This closing of the normally open circuit causes the signal transmitting portion 150 to send a signal to the generator 140 to display a message such as "Reprocessed device" on a display 160 as an explanation of the reason for the failure of the single-use device 10.

The shape-memory material 20 can be, in accordance with aspects of the invention, incorporated into the circuit portion 40 so as to function as a heat-activated electrical switch. The switch can either close or open the disabling/enabling circuit. The closing or opening the disabling/enabling circuit causes the device into which the switch is incorporated to be disabled. Optionally, the actuation of the switch can cause an indication of the disabled condition to be made.

What has been described and illustrated herein are preferred embodiments of the invention along with some variations. The terms, descriptions and figures used herein are set forth by way of illustration only and are not meant as limitations. Those skilled in the art will recognize that many variations are possible within the spirit and scope of the invention.

What is claimed is:

1. An electronic surgical apparatus comprising:
   a circuit portion that is configured to control an operation of the electronic surgical apparatus; and
   a shape-memory material, the shape-memory material having a property such that the shape-memory material assumes a predetermined shape when the electronic surgical apparatus is heated to a transition temperature,
wherein the shape-memory material disables the electronic surgical apparatus by acting on the circuit portion when the shape-memory material assumes the predetermined shape such that the electronic surgical apparatus will not perform the operation even when the circuit portion is supplied with energy.

2. The electronic surgical apparatus according to claim 1, wherein the shape-memory material is configured such that, upon assuming the predetermined shape, the shape-memory material opens a circuit in the circuit portion to disable the electronic surgical apparatus.

3. The electronic surgical apparatus according to claim 1, wherein the shape-memory material is configured such that, upon assuming the predetermined shape, the shape-memory material completes a circuit in the circuit portion to disable the electronic surgical apparatus.

4. The electronic surgical apparatus according to claim 1, wherein
the shape-memory material is nitinol.

5. The electronic surgical apparatus according to claim 1, wherein
the transition temperature is below a sterilization temperature of the electronic surgical apparatus.

6. The electronic surgical apparatus according to claim 1, further comprising:
a movable blocking element that is disposed adjacent to the shape-memory material and extends out of the electronic surgical apparatus, wherein
the movable blocking element is configured to block the shape-memory material from assuming the predetermined shape prior to moving the movable blocking element from a blocking position.

7. The electronic surgical apparatus according to claim 6, wherein
the movable blocking element is attached to a packaging of the electronic surgical apparatus such that the movable blocking element is moved from the blocking position upon removing the electronic surgical apparatus from the packaging.

8. The electronic surgical apparatus according to claim 6, wherein
the movable blocking element includes an elongated portion that inhibits use of the electronic surgical apparatus if the movable blocking element is not removed from the electronic surgical apparatus prior to use.

9. The electronic surgical apparatus according to claim 8, further comprising a shaft portion, wherein
the elongated portion of the movable blocking element includes a ring like portion that is disposed at least partially around the shaft portion.

10. The electronic surgical apparatus according to claim 8, further comprising an operation button, and the elongated portion of the movable blocking element includes a flange portion that is configured to inhibit operation of the operation button prior to removal of the movable blocking element from the electronic surgical apparatus.

11. The electronic surgical apparatus according to claim 6, wherein
at least a portion of the movable blocking element is flexible, and
a removal path of the movable blocking element is non-linear, thereby inhibiting reinsertion of the movable blocking element after removal.

12. The electronic surgical apparatus according to claim 6, further comprising:
at least one movable portion that moves to a blocked position to block return of the movable blocking element to the blocking position after the movable blocking element has been removed from the blocking position.

13. The electronic surgical apparatus according to claim 6, wherein
at least one portion of the movable blocking element is a pin that is removed from the electronic surgical apparatus when the movable blocking element is moved out of the blocking position.

14. The electronic surgical apparatus according to claim 1, wherein
the electronic surgical apparatus is configured to apply energy to tissue, and the circuit portion includes an energy-controlling circuit of the electronic surgical apparatus.

15. The electronic surgical apparatus according to claim 1, wherein
the electronic surgical apparatus is configured to cut tissue, and the circuit portion includes a cutting-controlling circuit of the electronic surgical apparatus.

16. An electronic apparatus comprising:
a circuit portion that is configured to control an operation of the electronic apparatus; and
a heat-activated electrical switch comprising a shape-memory material included in the circuit portion that moves to a predetermined position when the electronic apparatus is heated above a predetermined temperature to disable the electronic apparatus such that the electronic apparatus will not perform the operation even when the circuit portion is supplied with energy.

17. The electronic apparatus according to claim 16, wherein
the electronic apparatus is an electronic surgical apparatus, and the predetermined temperature is below a sterilization temperature of the electronic surgical apparatus.

18. An electronic apparatus comprising:
a circuit portion that is configured to control an operation of the electronic apparatus; and
a heat-activated electrical switch included in the circuit portion that moves to a predetermined position when the electronic apparatus is heated above a predetermined temperature to disable the electronic apparatus; and
a movable blocking element that is disposed adjacent to the heat-activated electrical switch and extends out of the electronic apparatus, wherein
the movable blocking element is configured to block the heat-activated electrical switch from moving to the predetermined position prior to moving the movable blocking element out of a blocking position.

19. A single-use electronic surgical apparatus comprising:
a circuit portion that is configured to control an operation of the electronic surgical apparatus;
a shape-memory material, the shape-memory material having a property such that the shape-memory material assumes a predetermined shape when the electronic surgical apparatus is heated to a transition temperature; and
a signal transmitting portion,
wherein the shape-memory material disables the electronic surgical apparatus by acting on the circuit portion when the shape-memory material assumes the predetermined shape such that the electronic surgical apparatus will not perform the operation even when the circuit portion is supplied with energy, and
the signal transmitting portion sends a signal to a display unit to indicate that the single-use electronic surgical apparatus is disabled due to being reprocessed when the shape-memory material assumes the predetermined shape.

20. An electronic apparatus comprising:

a circuit portion that is configured to control an operation of the electronic apparatus; and a shape-memory material, the shape-memory material having a property such that the shape-memory material assumes a predetermined shape when the electronic apparatus is heated to a transition temperature, wherein the shape-memory material disables the electronic apparatus by acting on the circuit portion when the shape-memory material assumes the predetermined shape such that the electronic apparatus will not perform the operation even when the circuit portion is supplied with energy.

* * * * *